United States Patent [19]
Johnston

[11] Patent Number: 6,023,932
[45] Date of Patent: Feb. 15, 2000

[54] TOPICAL COOLING DEVICE

[76] Inventor: Robert Johnston, 4945 Baldwin Street S, Brooklin, Canada, L0B 1C0

[21] Appl. No.: 09/139,868

[22] Filed: Aug. 25, 1998

Related U.S. Application Data

[60] Provisional application No. 60/056,783, Aug. 25, 1997.

[51] Int. Cl.[7] .................................................. F25B 21/02
[52] U.S. Cl. .......................... 62/3.5; 62/3.2; 62/3.7; 62/259.3; 607/96
[58] Field of Search .............................. 62/3.2, 3.7, 3.5, 62/259.3; 607/96

[56] References Cited

U.S. PATENT DOCUMENTS

| | | | |
|---|---|---|---|
| 5,419,780 | 5/1995 | Suski | 136/205 |
| 5,603,220 | 2/1997 | Seaman | 62/3.7 |
| 5,623,868 | 4/1997 | Harrington | 62/3.2 |

*Primary Examiner*—Henry Bennett
*Assistant Examiner*—Mark Shulman
*Attorney, Agent, or Firm*—Eric Fincham

[57] ABSTRACT

A portable topical heat transfer device for topically cooling an animal or human when required such as to relieve pain and swelling from injured joints or muscles or the like. The device comprises a thermoelectric unit having a cold side and a warm side, a DC source which is connected to the thermoelectric unit, a heat sink which is mounted in a heat conductive relationship with the warm side of the thermoelectric unit, a fan for removing heat from the heat sink, and a strap or the like for securing the device to the body of a person.

8 Claims, 2 Drawing Sheets

TOPICAL COOLING DEVICE

This application claims benefits of provisional application 60,056,783 filed Aug. 25, 1997.

BACKGROUND OF THE INVENTION

The invention relates to a method and a device suitable for topically cooling an animal or human, or more specifically, a cryotherapy unit for use in physical therapy, orthopedics, rhumatology, chiropractic treatments, sports medicine and veterinary medicine to relieve pain and swelling from injured or diseased joints, muscles and connective tissues and to promote healing.

Localized hypothermal or cryopractic treatment (topical application of cold to selected parts of the body) has gained wide acceptance for treatment of occupational and sports injuries. Cold treatment has proven successful in reducing pain and swelling.

Cold therapy calls upon a variety of devices that are inconvenient and/or uncomfortable to use. The most common device is a piece of ice applied either directly or wrapped in a cloth and applied to the site. The ice melts and must be frequently replaced. In the process of melting, dripping water must be contended with. Patients usually loose patience with the remedy.

Ice packs or their replacements of various materials can be placed in the freezer for a few hours before applying to the injured site. Their advantage is their low cost and that they do not drip. The inconvenience is that they do not stay cold very long and must be refreshed. They also cover an area much larger than the injury site. Cooling an area around the injury reduces blood flow and can result in collateral damage. Ice packs typically are at a temperature of approximately −17° C. and as a result there is a risk of tissue damage at the contact site between flesh and a device at −17° C. At the very least, it is uncomfortably cold for most patients.

Immersing a part of the body in a bath of ice water or other cold liquid is another option. This is practical for limited parts of the body such as hands, elbows and feet. A patient cannot be mobile while using such a device. There is also the risk of cooling the whole area and causing collateral damage. The application feels uncomfortably cold to most patients.

Mechanical and electrical devices have been used to cool a fluid or air that is conducted to the area to be treated. These devices tend to be large and cumbersome and as a result these devices are usually restricted to use in the office of a medical therapeutic practitioner.

Ideally, cryotherapy should begin as soon after the injury as possible and continue for two or three days, and in some cases two or three weeks. The cold should be applied for a period of about 20 minutes followed by a period of about 20 minutes where the body location is allowed to regain normal temperature. The treatment ideally should be 24 hours a day.

SUMMARY OF THE INVENTION

It is an object of the present invention to provide a method for the topical cooling of an animal or a human.

It is a further object of the present invention to provide portable topical heat transfer device which may be used for topically cooling an animal or a human.

It is a still further object of the present invention to provide a portable topical heat transfer device suitable for the treatment of a medical condition, and which device is compact and can cool a relatively small area.

According to one aspect of the present invention, there is provided a portable topical heat transfer device comprising a thermoelectric unit having a cold side and a warm side, electric power means connected to the thermoelectric unit, a heat sink mounted in a heat conductive relationship with the warm side of the thermoelectric unit, fan means for removing heat from the heat sink and means for securing the heat transfer device to the body of a person.

According to a further aspect of the present invention, there is provided a method for topically cooling a part of a body, the method comprising the step of supplying a heat transfer device comprising a thermoelectric unit having a cold side and a warm side, electric power means connected to the thermoelectric unit, a heat sink mounted in a heat conductive relationship with the warm side of the thermoelectric unit, fan means for removing heat from the heat sink and supplying power to the electric power means while placing the cold side on a selected body portion, and securing the device to the body of a user.

In greater detail, the device supplies a direct current to a thermoelectric cell (an electronic heat pump or "Peltier" cell) which causes one side to become cold and the other side to become warm. The cold side is placed in contact with the part of the body to be cooled. The warm side of the thermoelectric cell is placed in contact with a heat sink. A fan blows ambient air across the fins of the heat sink to dissipate the heat into the surrounding air.

Preferably, an electronic control device monitors the cold side of the thermoelectric cell by a sensor. When the cold temperature drops to close to freezing temperature, the current to the thermoelectric cell is interrupted to allow the temperature to rise a couple of degrees before re-powering. Also, in the event that air supply to the fan should be blocked, a sensor may signal the control device to interrupt the power to the thermoelectric cell and sound an acoustic signal transducer until the temperature returns to a preset level.

The device may be designed to operate on battery power (preferably rechargeable) as well as through a power supply plugged into the mains. In order to ensure proper operation and to prevent damage to the batteries by over discharging, preferably the electronic control device monitors the battery voltage. When the voltage drops below a set value, the acoustic signal transducer emits a warning to replace the battery with a freshly recharged one. Continued operation with a partially discharged battery would further reduce the battery voltage until the control unit shuts the power off.

Experience indicates that the ideal duty cycle is preferably 20 minutes on and 20 minutes off. However, depending on the thickness of flesh between the surface and the injured site it may be desirable to alter the duty cycle. The control unit may be equipped with a selector switch that can vary the duty cycle timer to match the needs of a particular patient or injury. The fan could be fitted with a weight that causes the unit to vibrate and provide a soothing massage effect that enhances blood flow to the injured area. Preferably, the control unit is mounted on the heat sink beside the fan to make a compact assembly. An on/off switch is provided to shut the unit on or off or to restart the duty cycle at the "on" part of the cycle.

In one particular embodiment, the thermoelectric cell has a smaller surface than the heat sink to which it is attached. The warm underside of the heat sink is also in contact with the skin and warms the surrounding area. Also the warm air exits the heat sink on all four edges. The escaping warm air tends to warm the surrounding flesh. The warmth contributes to increased blood circulation around the injury site while the thermoelectric cell cools the actual injury. This further accelerates healing. For most patients, this warmth also contributes to them being unaware of the cold after about three minutes of the unit being turned on even though the cold temperature is near freezing.

For certain bony parts of the body surface contact can be increased by providing an interface material between the cold side of the thermoelectric cell and the body. The interface piece may be either soft and pliable to take the form of the area or it may be premolded.

The interface between the cold side of the thermoelectric cell and the point of application may be several centimeters and may also have multiple points of contact such as one point of contact for each knuckle of the hand.

BRIEF DESCRIPTION OF THE DRAWINGS

Having thus generally described the invention, reference will be made to the accompanying drawings illustrating an embodiment thereof, in which.

DESCRIPTION OF THE PREFERRED EMBODIMENTS

Figure 1:
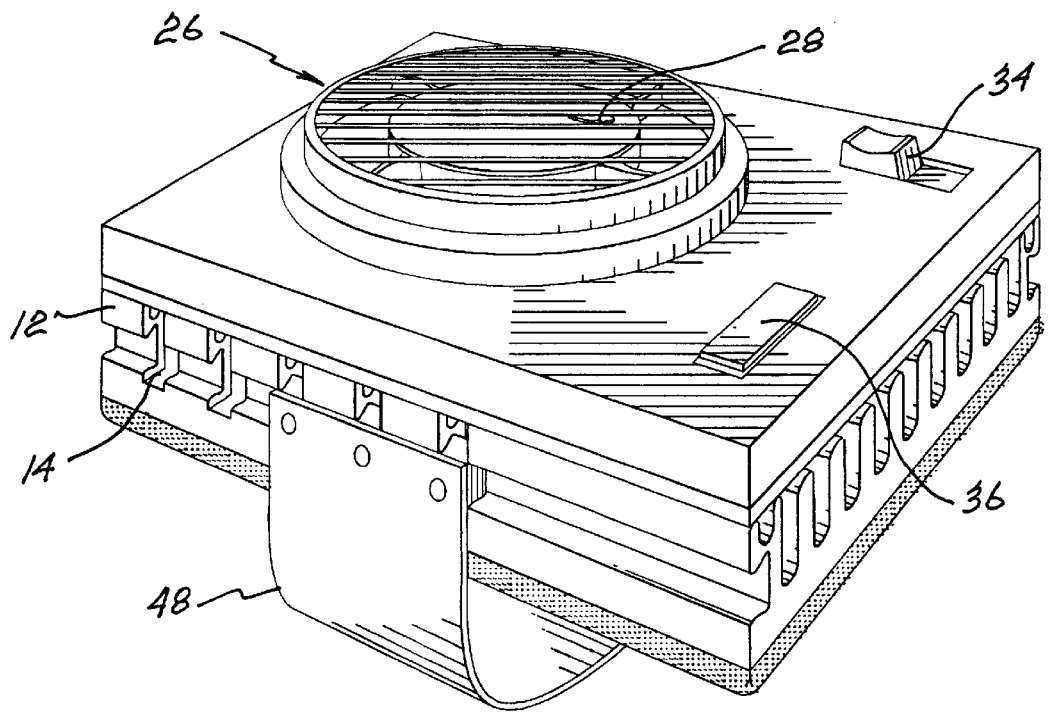
FIG. 1 is perspective view of one embodiment of a device according to the present invention.
Figure 2:
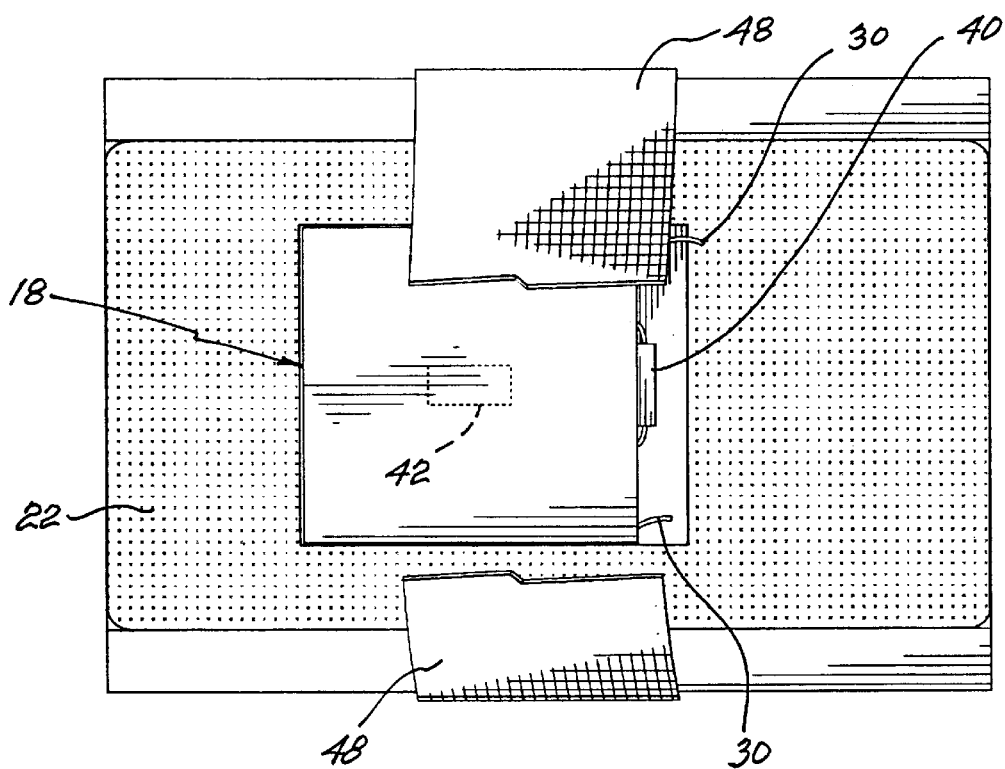
FIG. 2 is a bottom plan view thereof with a portion of the strap cut away and illustrating hidden components in dotted lines.
Figure 3:
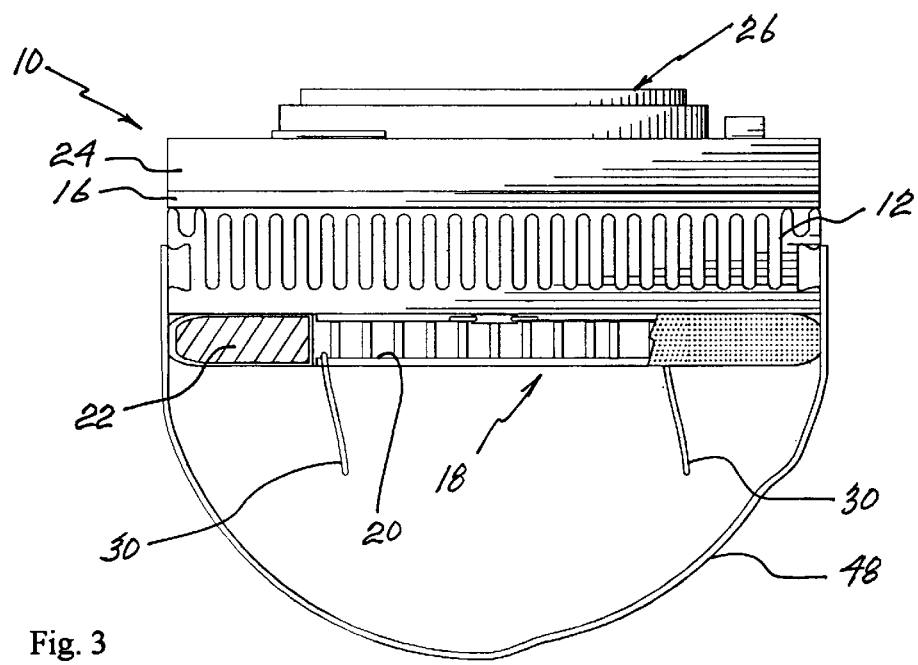
FIG. 3 is a side elevational view thereof.
Figure 4:
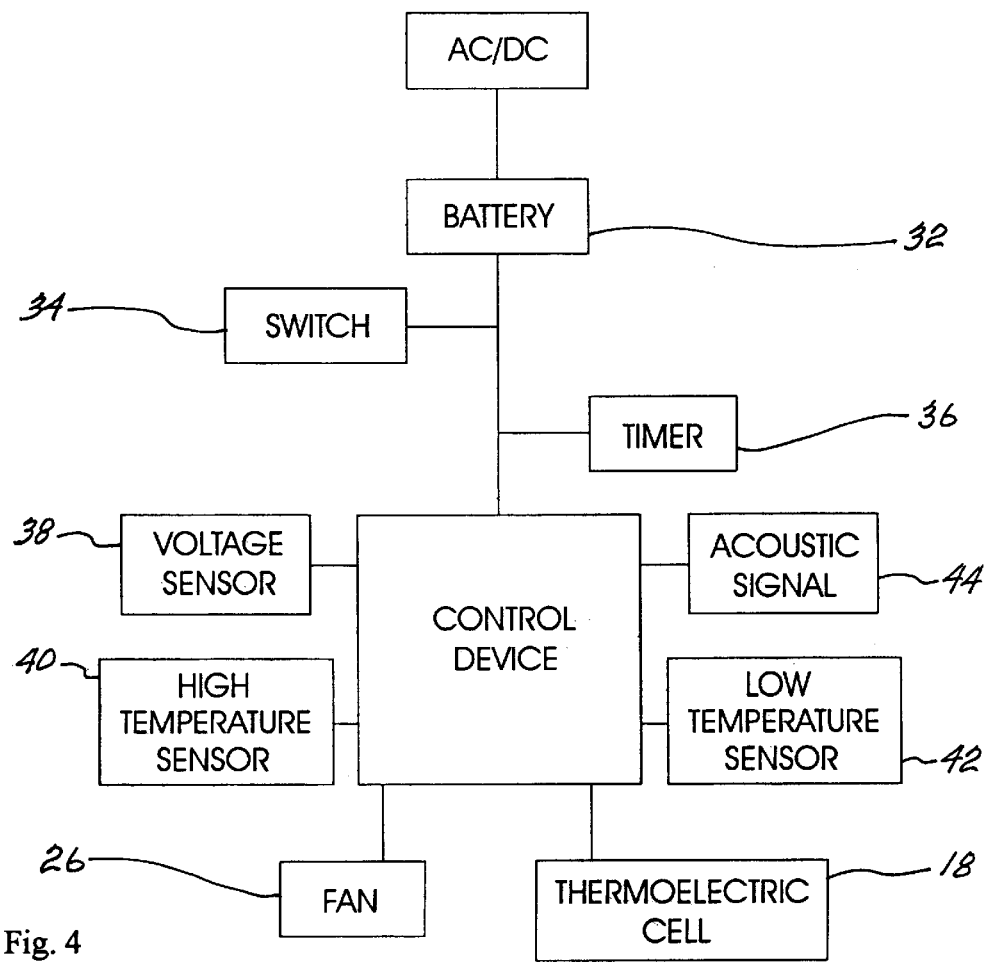
FIG. 4 is a schematic of a portion of the electric circuit.

Referring to the drawings in greater detail by reference characters thereto, there is illustrated a thermoelectric device according to one embodiment of the present invention and which device is generally designated by reference numeral 10.

Thermoelectric device 10 has a main body portion 12 designed to function as a heat sink and is thus made of a suitable metallic material. Heat sink 12 has a plurality of channels 14 extending therethrough to aid in the dissipation of the heat.

Mounted on the bottom of heat sink 12 is a thermoelectric "Peltier" cell generally designated by reference numeral 18. Mounted on top of heat sink 12 is a control device 16 which is encapsulated in a potting compound 24.

Thermoelectric cell 18 has a cold side 20 to which is secured a cushion material 22 which surrounds the thermoelectric cell.

Mounted on the top of heat sink 12 is a fan 26 to assist in the removal of the heat from heat sink 12. In the illustrated embodiment, a weight 28 is mounted on fan 26 such that operation of fan 26 will cause a vibration therein and which vibration is transmitted through the entire device 10.

Electric wires 30 connect the unit to a 6 volt battery or an alternate 6 volt power supply that is plugged into a conventional 110–125 volt AC outlet. A rechargeable battery 32 is provided for portable operation of the device.

The device includes a switch 34 for turning the device on or off. A timer selector 36 may be used to provide a duty cycle in an on/off mode. A voltage sensor 38 is provided to sense the voltage value and is coupled to an acoustic signal transducer 44 to emit a warning signal when the voltage drops below a preset value.

A high temperature sensor 40 and a low temperature sensor 42 are provided to send a signal when the minimum or maximum preset temperature is exceeded.

The device is shown with a strap 48 for securement to the body. In the illustrated embodiment, such a strap is attached to a channel in the side of body 12 and may be used for securing the device about a hand of a user. Other types of straps can naturally be employed.

It will be understood that the above described embodiment is for purposes of illustration only and that changes and modifications may be made thereto without departing from the spirit and scope of the invention.

I claim:

1. A portable topical heat transfer device for treating a body portion, said device comprising:

a thermoelectric unit having a cold side and a warm side, said cold side being located proximate an outer surface of said heat transfer device;

electric power means connected to said thermoelectric unit;

temperature sensing means for sensing the temperature of said cold side of said thermoelectric unit;

a heat sink, said heat sink being mounted in a heat conductive relationship with said warm side of said thermoelectric unit;

fan means for removing heat from said heat sink; and means for securing said heat transfer device to the body of a person such that said cold side can be placed adjacent said body portion to be treated.

2. The device of claim 1 wherein a portion of said heat sink surrounds said cold side of said thermoelectric unit such that when said cold side is placed in contact with a body portion for cooling the same, the area around said body portion is maintained at an elevated temperature.

3. The device of claim 1 wherein said temperature sensing means are operatively connected to shut off current to said device before the temperature thereof reaches 0° C.

4. The device of claim 1 further including timer means, said timer means being connected to said electric power means to turn on and shut off said electric power means.

5. The device of claim 1 wherein said fan further includes vibration means, said vibration means being operative to impart a vibration to said fan and said thermoelectric unit.

6. The device of claim 1 wherein said electric power means comprises battery means.

7. The device of claim 6 further including an acoustic signal means, said acoustic signal means being coupled to said device to emit a signal when voltage from said battery means drops below a predetermined level.

8. The device of claim 1 further including flexible thermally conductive means mounted on said cold side of said device.

* * * * *